United States Patent
Chen et al.

(10) Patent No.: US 9,328,363 B2
(45) Date of Patent: May 3, 2016

(54) **GENETICALLY ENGINEERED *YARROWIA LIPOLYTICA* WITH ENHANCED EXTRACELLULAR SECRETION OF α-KETOGLUTARATE**

(71) Applicants: Jian Chen, Wuxi (CN); Jingwen Zhou, Wuxi (CN); Hongwei Guo, Wuxi (CN); Guocheng Du, Wuxi (CN)

(72) Inventors: Jian Chen, Wuxi (CN); Jingwen Zhou, Wuxi (CN); Hongwei Guo, Wuxi (CN); Guocheng Du, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 44 days.

(21) Appl. No.: 14/142,897

(22) Filed: Dec. 29, 2013

(65) Prior Publication Data
US 2015/0104794 A1    Apr. 16, 2015

(30) Foreign Application Priority Data
Oct. 15, 2013    (CN) .......................... 2013 1 0481832

(51) Int. Cl.
*C12N 15/74*    (2006.01)
*C12N 1/20*    (2006.01)
*C12P 7/50*    (2006.01)
*C07K 14/39*    (2006.01)
*C12N 15/81*    (2006.01)
*C12N 1/16*    (2006.01)

(52) U.S. Cl.
CPC . *C12P 7/50* (2013.01); *C07K 14/39* (2013.01); *C12N 1/16* (2013.01); *C12N 15/815* (2013.01)

(58) Field of Classification Search
None
See application file for complete search history.

(56) References Cited

PUBLICATIONS

Coelho et al., "Yarrowia lipolytica: an industrial workhorse", in Current Research, Technology and Education Topics in Applied Microbiology and Microbial Biotechnology, A. Mendez-Vilas (Ed..), pp. 930-944, 2010.*
Blazeck et al., Nature Communications, 5, 3131, 2014.*

* cited by examiner

*Primary Examiner* — Nancy T Vogel
(74) *Attorney, Agent, or Firm* — Lili Chen

(57) ABSTRACT

The present invention provides four keto acid transporter encoding sequences selected from 6611 protein coding sequences of *Yarrowia lipolytica* CLIB122 database. Also provided are recombinant *Yarrowia lipolytica* strains overexpressing the keto acid transporters, which have increased extracellular secretion of α-ketoglutarate. The present invention can be used to increase extracellular levels of α-ketoglutarate during the fermentation process and lower downstream purification cost for α-ketoglutarate production.

4 Claims, 4 Drawing Sheets

Figure 2

SEQUENCE LISTING

<160> NUMBER OF SEQ ID NOS: 55

<210> SEQ ID NO 1
<211> LENGTH: 1590
<212> TYPE: DNA
<213> ORGANISM: Yarrowia lipolytica CLIB122

<400> SEQUENCE: 1

| | |
|---|---|
| atgcccatca cagtttcaca agaagtgacg gaaacagccc ccgaggtatc ttgggccgcc | 60 |
| accaagacct acctgggctc ccgtgtctct accctcaaac ctcccaagtt gtctgctcaa | 120 |
| gaaaaacgtt gcctgaatcc catctacgtg ctgcgtcagc tcggcaagaa acagtggctc | 180 |
| tttttctccg tggccatcct gggctggatc tgggacgcct tcgattactt ctctgtgtct | 240 |
| cagactgcga ccgagatcgc caaggatctc gacatgtctg tggcggacat cacctggggt | 300 |
| ctttctattg tgctcatgct gcgttcgatc ggagccatca tcttcggtct ggcctccgat | 360 |
| cgattcggac gtaagtggcc cttcatcgtc aacattgcca ttttctccat tctggagcta | 420 |
| ggaaccggct tgtgcaaac ctacacccag tttctggctt gcgtgcact gtttggaatc | 480 |
| gccatgggcg gcatgtttgg caacgctgcc gccactgccc tggaagactg tcccccgag | 540 |
| gctagaggtc tgatctcagg attcctccag gcaggctacg atatcggcaa cctgctctgt | 600 |
| gtgattttca cccgagcaat cgttcccaac tccaaacatg gctggagagc cctcttctgg | 660 |
| ttcggagctg gcctcctat tctcatcatg gtcttccgag cattcctgcc cgaaaccgat | 720 |
| acctatattg cctcccgaat caacaaggaa gacaacagca ccgtggaaat cgatcctgag | 780 |
| accggccttc acatgcagcc cgcccagaag gtgggaacct gggcctccat tgtcattttc | 840 |
| atcaagggtg tcggacacac actcaaggtc cactggctta tgttcaccta cctggttgtc | 900 |
| atgatggccg gtttcaactt tatggcccat ggctctcaag atctatatcc caccttgcta | 960 |
| aaaaaccagc tcaagttctc cattgaccgg tctactgtca ccaacgctgt tgccactctc | 1020 |
| ggtgctcttt cgggccaggt gactatcggc catctttcca acgtctttgg tcggcgactt | 1080 |
| tctgtgatca tctcctgcgt cattggagga gctctcatct accctgggc cttctctggc | 1140 |
| ggaggagccg gtatcaacgc ctctgtcttc ttcttgcagt tctttgttgg ctgctggggt | 1200 |
| atcgttccca tccacctgtc agagctgact cctcctgccc tgcgaacctc gcttgtcggt | 1260 |
| gtcgcctacc agctcggtaa cctggcgtct gctgcatctt ccactattga ggccaaaatc | 1320 |
| ggagagcggt tccctattct cgatgagcac ggaaaccacc tccctgagga gtatgattac | 1380 |
| ggcaaagtca tggccatttt catgggctgc gtgtttgcct tcaccatgat cgtcatgttc | 1440 |
| ctgggacccg agaagcgagg ctccgacctg tgtgctcctc agtacgaggt taccgacgcc | 1500 |
| cagacagccg ctggagacga aagttcgaa gacaaggaga aggtcgagga agttgccatc | 1560 |
| gaacgaatcg acaccaatct cactcgttaa | 1590 |

<210> SEQ ID NO 2
<211> LENGTH: 1500
<212> TYPE: DNA
<213> ORGANISM: Yarrowia lipolytica CLIB122

<400> SEQUENCE: 2

| | |
|---|---|
| atggatttgg acaacctccc tgccccagat ctttcgtgga agagcatcaa gcactacttg | 60 |
| gcaactcgag ttactacatt gaagcctcct aagctctctg cggaggagaa aaagcacatc | 120 |
| aaccctatcc ctgctcttcg gactcttaac aagaagcaat ggctgttgt tctctgtggt | 180 |
| ctggcgggtt ggacttggga ctcttttgat tttttcagtg tgtctctggt ggcctctgat | 240 |

```
atcgctaagg accttaatgt gagcgtcaca gatatcactt ggggtattac tcttgttctt      300
atgcttcggt ctgttggagc tatcatcttc ggtgttgctt ctgatcgtta tggtcgaaaa      360
tggccattca tcttcaactg tgttctattt attgtgctgg agcttggaac gggttttgtc      420
cagacctaca agcagttttt gggagtgcga gcattgtttg aatcgcaat gggaggtatt       480
tatggtaacg ctgctgcaac tgccttggag gactgtcccc ctgaggcccg aggtgttatt      540
tccggtctgt tgcaggaggg ttatgcgctg gttatttgc tttgtgtgat ctttactcga       600
gctattgcag acacatctcc tcatggatgg agagctctct tctggtttgg atcaggtccc      660
ccagttctca tcatcatctt tcgattcttc cttcctgaaa ccgataccta catccaatcg      720
aagcagaacg ccgaggcctt gggcgtcgag aaacattct ggttgggaat caaaactact       780
ttcaaaactt actggctcat gttcatctac cttgtggttc tcatggctgg cttcaacttc      840
atgtcccatg gatctcagga tctctacccc actatgctaa aggttcagct gggcttctct      900
cctgatcgat ctacggtcac caactgtgtt gctaatctcg cgctattgc tggtggtgtt       960
atcattggtc acttttcttc cgtgttaggt cggcgtcttt ctatcatgat ctcctgtatt     1020
cttggtggag ccatgattta cccttgggcc tttgtgacta actcgggaat taatgcaggt     1080
gttttcttct tgcagttctt cgtccagggt gcctggggcg tcattcccat tcatcttact     1140
gaactgtgtc cccagctctc tcgatcatcc ctggttggtt tggcctatca gcttggtaac     1200
ctcgcatctt cagcttcatc cactatcgaa gcccagattg gcacccaatt ccccatcaaa     1260
gatgataatg gggtcgaccg acccggtgtg tacaactact cttggtcat gtgcattttc      1320
atcgcctgtg ttttcaccct tgtttcgtg gttaccttc tgggcccga aacagaatg         1380
gctgagatgg ttgctcacga gcatgttgag tacactaagg agatgtctga tgatgaagag     1440
aagggtgtcc aagagactgt cgaggtcgtc gagagagttg acaccaatgc tactaagtag     1500
```

<210> SEQ ID NO 3
<211> LENGTH: 1572
<212> TYPE: DNA
<213> ORGANISM: Yarrowia lipolytica CLIB122

<400> SEQUENCE: 3

```
atggatctcg acaactaccc tcctcccgat ctctcatggt ctaacatcaa gcactacctg       60
ggcactcgaa tctccaccct gaagcccccg aagctcactg aggctgagaa gaaacacatg      120
aaccccatcc ctgccctgcg actgctcaac aagaagcagt ggctgttcgt gggtgtggct      180
cttgccggct ggacttggga cgcctttgac ttcttctccg tcggtgtggt cgctacgcag      240
atcgccgagg acctgaatgt cacagtcaag gatgtcacct ggggtatcac tctggtgctc      300
atgctgcgag ctgttggtgc tgttctgttt ggtgtggcct cggaccgata tggtcgaaaa      360
tggccctttta tcttcaacaa ctttctcttt gtcgtcctgg aactcggaac cggtttcgtg      420
cagacctacc agcagttcct gggagtccga gctctgtttg gtatcgctat gggtggtctc      480
tacggtaacg ctgctgccac tgctcttgaa gactgccctc ctgaagcccg aggttttatt      540
tctggtctct tccagaaggg ttacggtgta ggatacttgc tctgtgtcgt ttttgctcgt      600
gctattgcta atacttctcc ttacggctgg agagctctgt tctggttcgg agcctgtcct      660
cccgtgctca tcatgatctt tcgattcttc cttcccgaaa ccgacactta catccagtca      720
aagaagaacg ccgaggccga aggagttgag aaacaattct ggcagggagt caagaccacc      780
tttaagtcgt actggctcat gttcttctac ctggttctct tcatgaccgg cttcaacttc      840
```

```
ctttcccatg gctctcagga cctctacccc accatgctgc gagctcagct gggcttcgac    900
aaggatcagt ttaccatcac taactctgtt gcttctctgg gctccatctt cggtggaatg    960
gtcattggtc acgcgtcttt tattctcggc cgacgtctta ctattcttct ggcttgtatc   1020
ctcggtgctg cctgcatcta cccatgggcc tttgtcactg gtcccggtat caatgccgga   1080
gtcttcttcc tgcagttctt tgcccaggga gcttgggag tcgttcccat ccatctcacc   1140
gaactgtctc cccctgccct tcgatcttcc atgattggta ttgcctacca gctcggtaac   1200
ctggcctctt ccggttcttc taccatccag gccactatcg gtacccagtt ccctctgaga   1260
gacgagaacg gaaagatccg acccggtgtc tacaactact cgcttgtcat ggccatcttc   1320
attgcgtgtg tctttgtctt cctctttgtc gtcaccctgc ttggtcctga gcgacgacac   1380
gctgaaatga ttgctggtgg tgctggacac cgatccgagt ctgacgaaaa gatctacgac   1440
gaagagaagg gagctgctgt caatgttgaa caagtggaat cgcctgctag cactcctgaa   1500
cgttctgcta gcccgttgcc gaccacagag gtcaaccaca cctctgagac cctccccgga   1560
tcccaaaagt ga                                                       1572

<210> SEQ ID NO 4
<211> LENGTH: 1509
<212> TYPE: DNA
<213> ORGANISM: Yarrowia lipolytica CLIB122

<400> SEQUENCE: 4
atgaattttg caaacttccc agcaccagat ctgtctccaa agaacatcaa gaggtaccta     60
gtcactcgag tcacttcttt gaagcctcca aagctcacgg ttgaggaaaa aaagcacatc    120
aacccgattc ctgcccttcg acttctgaac aggaagcagt ggttgtttgt agctgtggga    180
ttctgtggct gggcttggga ctcgtttgat ttcttttctg tgtcgctggt tgcatctgaa    240
attgctgaga gtctccatgt gtctgtcaca agtatcacct ggggtatcac tcttgtgctc    300
atgttgcgat ctgttggagc tgtcatcttc ggaatgctgt cggatcgttt tggacgaaaa    360
tggccccttca tcaccaactg tgtcttgttt attgtcctgg aattgggcac cgggtttgta    420
cagacatata agcagttcct tgccgtcaga gctctgtttg gaatcgcaat ggggggtatc    480
tacggcatgg cagcagctac agccctcgaa gactgcccag tacaggccag aggagtcatt    540
tcggactgc tacaggaagg ctatgcattc ggatacttgt tgtgtgtcgt gttcacccga    600
gccattgccg atacttctcc ttttgggtgg cgcgctcttt tctggttcgg ttcgggtcct    660
cctgttctca tcatcatctt ccgactatgt cttcctgaaa ccgacaccta tcttctttct    720
aaaaagaacg cagcagaggc cgaaggtatt gaaaagaact ctggcgaggg catcaagatg    780
accttcaaga cgtactggct catgtttgcc tacctggttg ttctcatggg gggcttcaac    840
ttcatgtctc atggctcaca ggacttgtat ccgaccatgc tcaagaaaca gcttggattc    900
agcgaagacc gatctactgt taccaactgt gtggccaact ttggagctat tgccggtggc    960
cttgttgtgg gtcacgcttc ttcttttctt ggaagacgac tgtgtatcat gatctcttgt   1020
gtgatagggg gagcgctgat ctacccttgg gcctttgtca ccaacagtgg aatcaatgct   1080
ggagtcttct ttctgcagtt ttttgtccag ggagcctggg gagtcatccc tattcatctt   1140
acagagcttg cccctccggt ccttcgatcg tcaatggtag gggtggctta ccagctgggt   1200
aacctggctt cttctgcttc ttcaaccatt gaagccacta ttggagaaac atttcccctt   1260
tatgacaaat tcggaaacga aaaaccagga gtgtacaatt acagtctggt gatggccatt   1320
ttgatgggtt gtgtcttctt ttttgtgctt tgtgtcacgt ttctgggtcc agaaaacaga   1380
```

```
caagcagaga tgatctctgg aggctctgag caggataatg cctacgagag gaagctcgaa    1440
gagatggagg acgaagagaa agggtcact gagaacattg aaagacgttc ttcgagcgat    1500
actcgataa                                                            1509
```

<210> SEQ ID NO 5
<211> LENGTH: 1512
<212> TYPE: DNA
<213> ORGANISM: Yarrowia lipolytica CLIB122

<400> SEQUENCE: 5

```
atgacccagt cgtacgaagt cggaaacttg ccgcctccag atctgtcctg gagaagcgtc     60
aaaaggtacc tggccagtcg cgtgacgact ctgaaacctc aaccgctttc cgactcccag    120
aaacgtctcc ttaatccaat ccccacgctc cgtctgctca ccttcaaaca atggatgttc    180
gtgctggtgg ccttctgggg ctggacgtgg gacgcattcg acttctttc agtgtcgctg    240 gtggcttcgg agattgcaga aacactccag gtttccgtca cagacatcac gtggggcatc    300
accctggtgc tgatgctcag atccatcgga gcggtggtgt ttggagtgct gagtgataaa    360 tacgccgaa agtggccctt catctctaac ctggtgttgt ttatcgtgct ggagctcgga    420
acgggcttcg tcaccaccta caagcagttt ctcgccgtcc gagccctgtt tggaatcgcc    480
atgggcggga tctacggcat ggcagcagcc accgcgctgg aggattgtcc ggtcgatgcc    540
agaggcctcg tctcaggaat ccttcaggaa ggatacgccc tggggtactt gctgtgtgtg    600
gtcttcaccc gagctctcgt ctacacaact cccacggct ggcgatctct tttctggttc    660
ggtgccggcc ccccagtcct catcatcatc ttccgaatgg ccctgcccga aactgacacc    720
tatatccagt ccaagcacaa tgaagcggtg ctggatacgg gcaaaaactt ttttgtcggt    780
ctcaaaacga ctttcagcac ctattggctc acgttcatct acctggtgat tctcatgtcc    840
ggattcaact tcatgtccca tggctcccag gacctgtacc ccacgcggct caaaaaccag    900
ctggagttct cgcccgacgc ctccaccgtc accaactgcg tcgccaacct cggagccatc    960
gccggaggaa tctttatggg tcacatttcc tcgtttgccg gcagacggct gtgcatcatg   1020
atttcgtgcg tcgtgggagg cgctctcatc tatccctggg cgtttgtctc cagtaacgcc   1080
ggaatcaacg ccggcgtctt ctttctgcaa ttttgtgtcg ctggagcctg gggaatcatc   1140
cccatccatc tcaccgagct cgctcctcca gccctgcggt cttcgctcgt gggtctggcc   1200
taccagctgg gcaatctggc ctcctcggcg tcctccacca tcgaggcgaa aattggagag   1260
cggtttccgc tgactgacgc tcacggcaac gcccggccag gagtctacga ctacagtctg   1320
gtcatggcga ttctcatggg ctgcgtcttc ttttttgtgc tggtgtgcac attcctgggc   1380
cccgaaaaca gaaatgcgga gatggtggtc ggagagctcg taggccctga gaccaagctg   1440
gtcgaagacg aggcgatgga ggtctacgga gagcggcgtt ccgaacagac cactgttgga   1500
agtgttcatt ag                                                       1512
```

<210> SEQ ID NO 6
<211> LENGTH: 1575
<212> TYPE: DNA
<213> ORGANISM: Yarrowia lipolytica CLIB122

<400> SEQUENCE: 6

```
atggaagctc ctaatctctc gccagcttcc atcggcggt acttcgccac aagattgcct     60
actctcatcc cacaaaagct cacacctgaa gagaagaagc tcctcaaccc cttccctgcc    120
```

```
ctggctctta tcaacaagaa gacttggctc tttattgcat gcgctttctg cggttggact    180
tgggacgctt ttgatttctt ctcggtaggt ctagtggctc ccgaaattgc caaatctctt    240
aacagatccg tcaccgatat tacttggggt atcactttgg ttcttatgct tcgatctatt    300
ggtgctgttg ttttggtat tgcttccgat cgttacggac gaaagtggcc ctttattgtc     360
aacctgctgt gtttcattgc tctcgagctg ggatctgggt ttgttcagac ttacaaacag    420
tttcttggtg tccgagccat ctacggtatt gctatgggtg gtctttacgg taacgccgct    480
gctactgctc ttgaagattg tcctcctcaa gcacgaggta tcatttcagg tttccttcag    540
agtggatacg ccctgggtta cttgctttgt gtggtattca ctcgagctat tgctgatact    600
tctccttacg gatggagagc tctcttctgg ttcggctctg gaccccagt tcttttcatt     660 atcttccgat acttcctgcc tgaaactgaa acctaccttg cttccaaggc gtctcaggag    720
gaagctggaa tcgagaagaa gttctggaat ggaatcaagg ttactttcaa aaactactgg    780
ctcatgttta tctaccttgt tattctcatg gcaggcttca acttcatgtc ccacggctct    840
caagacctct accccactat gctcaagaac cagcgtcatt ttagcgctga ccgaagcact    900
gttaccaact gtgttgccaa ctttggtgca attgccggcg gtatgttgat tggtcacttt    960
tctactgctc tcggtcgacg actctccatc atgatctctt gtgttattgg aggtgctctg   1020
atttaccctt gggcctttgt tggcaactct gcaggaacaa atgcaggcgt tttttcctc    1080 caatttttcg ttcagggtgc ttggggtgtt gttcccattc atcttccga gttgtctcct    1140 cctgagcttc gatcttccat ggttggtatt gcctaccaga tgggtaacct ggcttcttct   1200
gcatcctcca ctatcgagtc taagatcggt gaacgattcc ctctgaagaa cgcgaagggg   1260
gagttcgaga agggtttcta tgattacggt aaggttatgg ccatcttcat gggctgcgtg   1320
ttcgggtttg ttcttattgt aacatttgtt gggcccgaga accgaggagc caccatgctt   1380
actgaggacg ctcagatgat ggtcgatgcg gagcacagac tggacgccga ggagaagggt   1440
gacttcgaga acttgagcg agtcgactca gagggcaagc agatggacaa ctttgttgaa   1500
gaggtcgctg agcctgaggg cgtgtacact ggttctcacc ctccccaata tgactccccc   1560
tacgagtcca agtaa                                                    1575
```

<210> SEQ ID NO 7
<211> LENGTH: 18
<212> TYPE: DNA
<213> ORGANISM: Artificial Sequence
<220> FEATURE:
<223> OTHER INFORMATION: PCR primer

<400> SEQUENCE: 7
caacaaggaa gacaacag                                                    18

<210> SEQ ID NO 8
<211> LENGTH: 18
<212> TYPE: DNA
<213> ORGANISM: Artificial Sequence
<220> FEATURE:
<223> OTHER INFORMATION: PCR primer

<400> SEQUENCE: 8
aggtaggtga acataagc                                                    18

<210> SEQ ID NO 9
<211> LENGTH: 19
<212> TYPE: DNA
<213> ORGANISM: Artificial Sequence

```
<220> FEATURE:
<223> OTHER INFORMATION: PCR primer

<400> SEQUENCE: 9
gcaaccatct cagccattc                                                    19

<210> SEQ ID NO 10
<211> LENGTH: 19
<212> TYPE: DNA
<213> ORGANISM: Artificial Sequence
<220> FEATURE:
<223> OTHER INFORMATION: PCR primer

<400> SEQUENCE: 10
gtaacctcgc atcttcagc                                                    19

<210> SEQ ID NO 11
<211> LENGTH: 19
<212> TYPE: DNA
<213> ORGANISM: Artificial Sequence
<220> FEATURE:
<223> OTHER INFORMATION: PCR primer

<400> SEQUENCE: 11
gcagacctac cagcagttc                                                    19

<210> SEQ ID NO 12
<211> LENGTH: 20
<212> TYPE: DNA
<213> ORGANISM: Artificial Sequence
<220> FEATURE:
<223> OTHER INFORMATION: PCR primer

<400> SEQUENCE: 12
acgacacaga gcaagtatcc                                                   20

<210> SEQ ID NO 13
<211> LENGTH: 19
<212> TYPE: DNA
<213> ORGANISM: Artificial Sequence
<220> FEATURE:
<223> OTHER INFORMATION: PCR primer

<400> SEQUENCE: 13
tgctacagga aggctatgc                                                    19

<210> SEQ ID NO 14
<211> LENGTH: 22
<212> TYPE: DNA
<213> ORGANISM: Artificial Sequence
<220> FEATURE:
<223> OTHER INFORMATION: PCR primer

<400> SEQUENCE: 14
ggaagatgat gatgagaaca gg                                                22

<210> SEQ ID NO 15
<211> LENGTH: 18
<212> TYPE: DNA
<213> ORGANISM: Artificial Sequence
<220> FEATURE:
<223> OTHER INFORMATION: PCR primer

<400> SEQUENCE: 15
ctgcttgtag gtggtgac                                                     18
```

-continued

```
<210> SEQ ID NO 16
<211> LENGTH: 21
<212> TYPE: DNA
<213> ORGANISM: Artificial Sequence
<220> FEATURE:
<223> OTHER INFORMATION: PCR primer

<400> SEQUENCE: 16
gagtgctgag tgataaatac g                                              21

<210> SEQ ID NO 17
<211> LENGTH: 23
<212> TYPE: DNA
<213> ORGANISM: Artificial Sequence
<220> FEATURE:
<223> OTHER INFORMATION: PCR primer

<400> SEQUENCE: 17
tctatgatta cggtaaggtt atg                                            23

<210> SEQ ID NO 18
<211> LENGTH: 18
<212> TYPE: DNA
<213> ORGANISM: Artificial Sequence
<220> FEATURE:
<223> OTHER INFORMATION: PCR primer

<400> SEQUENCE: 18
gactcgctca aggttctc                                                  18

<210> SEQ ID NO 19
<211> LENGTH: 21
<212> TYPE: DNA
<213> ORGANISM: Artificial Sequence
<220> FEATURE:
<223> OTHER INFORMATION: PCR primer

<400> SEQUENCE: 19
aagtccaacc gagagaagat g                                              21

<210> SEQ ID NO 20
<211> LENGTH: 21
<212> TYPE: DNA
<213> ORGANISM: Artificial Sequence
<220> FEATURE:
<223> OTHER INFORMATION: PCR primer

<400> SEQUENCE: 20
accagagtca agaacgatac c                                              21

<210> SEQ ID NO 21
<211> LENGTH: 19
<212> TYPE: DNA
<213> ORGANISM: Artificial Sequence
<220> FEATURE:
<223> OTHER INFORMATION: PCR primer

<400> SEQUENCE: 21
cgtttgccag ccacagatt                                                 19

<210> SEQ ID NO 22
<211> LENGTH: 19
<212> TYPE: DNA
<213> ORGANISM: Artificial Sequence
<220> FEATURE:
<223> OTHER INFORMATION: PCR primer
```

<400> SEQUENCE: 22
gcgtttgcca gccacagat                                                    19

<210> SEQ ID NO 23
<211> LENGTH: 19
<212> TYPE: DNA
<213> ORGANISM: Artificial Sequence
<220> FEATURE:
<223> OTHER INFORMATION: PCR primer

<400> SEQUENCE: 23
gtagatgcag gcagcaccg                                                    19

<210> SEQ ID NO 24
<211> LENGTH: 21
<212> TYPE: DNA
<213> ORGANISM: Artificial Sequence
<220> FEATURE:
<223> OTHER INFORMATION: PCR primer

<400> SEQUENCE: 24
aagacagagg cgttgatacc g                                                 21

<210> SEQ ID NO 25
<211> LENGTH: 20
<212> TYPE: DNA
<213> ORGANISM: Artificial Sequence
<220> FEATURE:
<223> OTHER INFORMATION: PCR primer

<400> SEQUENCE: 25
tgcgaggtta ccaagctgat                                                   20

<210> SEQ ID NO 26
<211> LENGTH: 19
<212> TYPE: DNA
<213> ORGANISM: Artificial Sequence
<220> FEATURE:
<223> OTHER INFORMATION: PCR primer

<400> SEQUENCE: 26
gacaaacgcc cagggatag                                                    19

<210> SEQ ID NO 27
<211> LENGTH: 19
<212> TYPE: DNA
<213> ORGANISM: Artificial Sequence
<220> FEATURE:
<223> OTHER INFORMATION: PCR primer

<400> SEQUENCE: 27
tgtccatctg cttgccctc                                                    19

<210> SEQ ID NO 28
<211> LENGTH: 13
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (6)..(6)

```
<223> OTHER INFORMATION: Xaa can be any naturally occurring amino acid
<220> FEATURE:
<221> NAME/KEY: misc_feature
<222> LOCATION: (10)..(12)
<223> OTHER INFORMATION: Xaa can be any naturally occurring amino acid

<400> SEQUENCE: 28

Asn Xaa Xaa Ser His Xaa Ser Gln Asp Xaa Xaa Xaa Thr
1               5                   10

<210> SEQ ID NO 29
<211> LENGTH: 51
<212> TYPE: PRT
<213> ORGANISM: Aspergillus flavus

<400> SEQUENCE: 29

Glu Gly Lys Thr Ala Leu Lys Arg His Trp Leu Leu Ile Tyr Leu
1               5                   10                  15

Val Leu Leu Met Ala Gly Phe Asn Phe Met Ser His Gly Ser Gln Asp
            20                  25                  30

Leu Tyr Pro Thr Leu Leu Lys Ser Glu Phe Ser Phe Ser Ala Asn Ala
        35                  40                  45

Val Thr Val
        50

<210> SEQ ID NO 30
<211> LENGTH: 51
<212> TYPE: PRT
<213> ORGANISM: Eremothecium gossypii

<400> SEQUENCE: 30

Gln Ile Trp Asn Ser Leu Trp Asn Glu Arg Tyr Ile Val Ile Tyr Met
1               5                   10                  15

Ile Leu Leu Met Thr Gly Tyr Asn Tyr Phe Ser His Ala Ser Gln Asp
            20                  25                  30

Leu Phe Pro Thr Met Leu Ile Lys Gln Leu Gly Tyr Ser Pro Asn Gln
        35                  40                  45

Ser Ala Val
        50

<210> SEQ ID NO 31
<211> LENGTH: 51
<212> TYPE: PRT
<213> ORGANISM: Aspergillus fumigatus

<400> SEQUENCE: 31

Glu Thr Lys Gln Met Leu Gly Lys Glu Trp Lys Met Cys Ile Tyr Cys
1               5                   10                  15

Val Phe Leu Met Thr Trp Phe Asn Tyr Tyr Ser His Thr Ser Gln Asp
            20                  25                  30

Ser Tyr Thr Thr Phe Met Leu Thr Gln Lys Glu Met Arg Asn Asp Gly
        35                  40                  45

Ala Ser Arg
        50

<210> SEQ ID NO 32
<211> LENGTH: 51
<212> TYPE: PRT
<213> ORGANISM: Eremothecium gossypii

<400> SEQUENCE: 32
```

Gln Ile Leu Arg Ser Leu Lys Lys Glu Trp Tyr Ile Ala Ile Tyr Met
1               5                   10                  15

Val Cys Leu Met Ala Gly Tyr Asn Phe Phe Ser His Ala Ser Gln Asp
            20                  25                  30

Leu Phe Pro Thr Met Leu Leu Lys Gln Leu Gly Tyr Ser Ser Asn Gln
            35                  40                  45

Ser Thr Leu
    50

<210> SEQ ID NO 33
<211> LENGTH: 50
<212> TYPE: PRT
<213> ORGANISM: Kluyveromyces lactis

<400> SEQUENCE: 33

Val Lys Lys Thr Val Ser Lys Tyr Trp Leu Leu Phe Gly Tyr Leu Ile
1               5                   10                  15

Leu Leu Leu Val Gly Pro Asn Tyr Leu Thr His Ala Ser Gln Asp Leu
            20                  25                  30

Phe Pro Thr Met Leu Arg Ala Gln Leu Arg Phe Ser Glu Asp Ala Val
            35                  40                  45

Thr Val
    50

<210> SEQ ID NO 34
<211> LENGTH: 50
<212> TYPE: PRT
<213> ORGANISM: Saccharomyces cerevisiae

<400> SEQUENCE: 34

Met Lys Arg Thr Val Gln Lys Tyr Trp Leu Phe Ala Tyr Leu Val
1               5                   10                  15

Val Leu Leu Val Gly Pro Asn Tyr Leu Thr His Ala Ser Gln Asp Leu
            20                  25                  30

Leu Pro Thr Met Leu Arg Ala Gln Leu Gly Leu Ser Lys Asp Ala Val
            35                  40                  45

Thr Val
    50

<210> SEQ ID NO 35
<211> LENGTH: 51
<212> TYPE: PRT
<213> ORGANISM: Debaryomyces hansenii

<400> SEQUENCE: 35

Gln Ile Ser Ser Val Phe Lys Thr Glu Trp Leu Met Phe Val Tyr Leu
1               5                   10                  15

Val Val Leu Met Ser Gly Tyr Asn Phe Met Ser His Gly Ser Gln Asp
            20                  25                  30

Leu Tyr Pro Thr Leu Leu Val Lys Gln His Asn Val Gly Pro Asp Arg
            35                  40                  45

Lys Thr Val
    50

<210> SEQ ID NO 36
<211> LENGTH: 51
<212> TYPE: PRT
<213> ORGANISM: Debaryomyces hansenii

<400> SEQUENCE: 36

```
Asn Ile Phe Thr Met Ile Lys Thr Glu Gly Leu Met Phe Val Tyr Leu
1               5                   10                  15

Val Leu Phe Ala Ala Gly Ile His Phe Thr Ser His Gly Ser Ala Asp
            20                  25                  30

Leu Tyr Pro Thr Phe Leu Val Lys Gln His Asp Ile Gly Ser Asp Arg
        35                  40                  45

Lys Thr Val
    50
```

<210> SEQ ID NO 37
<211> LENGTH: 51
<212> TYPE: PRT
<213> ORGANISM: Candida albicans

<400> SEQUENCE: 37

```
Ser Ile Leu Val Thr Phe Lys Thr Glu Trp Leu Ile Phe Ser Tyr Leu
1               5                   10                  15

Val Leu Leu Tyr Ala Gly Trp Asn Phe Thr Thr His Gly Ser Gln Asp
            20                  25                  30

Leu Tyr Val Thr Met Ile Thr Lys Gln Tyr His Val Gly Leu Asp Lys
        35                  40                  45

Lys Thr Val
    50
```

<210> SEQ ID NO 38
<211> LENGTH: 51
<212> TYPE: PRT
<213> ORGANISM: Candida albicans

<400> SEQUENCE: 38

```
Gln Ala Lys Lys Ala Leu Asn Gln Tyr Trp Leu Ile Ile Val Tyr Leu
1               5                   10                  15

Ile Phe Leu Met Ala Gly Phe Asn Phe Ser Ser His Gly Ser Gln Asp
            20                  25                  30

Leu Tyr Pro Thr Met Leu Thr Lys Gln Tyr His Tyr Gly Lys Asp Lys
        35                  40                  45

Ser Thr Val
    50
```

<210> SEQ ID NO 39
<211> LENGTH: 51
<212> TYPE: PRT
<213> ORGANISM: Yarrowia lipolytica

<400> SEQUENCE: 39

```
Gly Ile Lys Val Thr Phe Lys Asn Tyr Trp Leu Met Phe Leu Tyr Leu
1               5                   10                  15

Val Ile Leu Met Ala Gly Phe Asn Phe Met Ser His Gly Ser Gln Asp
            20                  25                  30

Leu Tyr Pro Thr Met Leu Lys Asn Gln Arg His Phe Ser Ala Asp Arg
        35                  40                  45

Ser Thr Val
    50
```

<210> SEQ ID NO 40
<211> LENGTH: 51
<212> TYPE: PRT
<213> ORGANISM: Aspergillus fumigatus

```
<400> SEQUENCE: 40

Asp Ser Gly Thr Ala Leu Lys Glu Asn Trp Val Leu Phe Ile Tyr Leu
1               5                   10                  15

Val Val Leu Met Thr Gly Phe Asn Ser Cys Ser His Gly Ser Gln Asp
            20                  25                  30

Phe Tyr Pro Thr Phe Leu Lys Asp Gln Val Gly Leu Gln Pro Thr Gln
        35                  40                  45

Val Thr Val
    50

<210> SEQ ID NO 41
<211> LENGTH: 51
<212> TYPE: PRT
<213> ORGANISM: Aspergillus oryzae

<400> SEQUENCE: 41

Glu Thr Lys Gln Met Leu Gly Gln Glu Trp Lys Met Cys Val Tyr Ala
1               5                   10                  15

Ile Ile Leu Met Thr Trp Phe Asn Tyr Tyr Ser His Thr Ser Gln Asp
            20                  25                  30

Ser Tyr Thr Thr Phe Met Leu Thr Gln Lys Gly Met Glu Asn Ala Gly
        35                  40                  45

Ala Ser Arg
    50

<210> SEQ ID NO 42
<211> LENGTH: 51
<212> TYPE: PRT
<213> ORGANISM: Kluyveromyces lactis

<400> SEQUENCE: 42

Asn Ala Lys Leu Ala Cys Ser Gln Tyr Trp Leu Ser Met Ile Tyr Leu
1               5                   10                  15

Val Leu Leu Trp Ala Gly Phe Asn Phe Ser Ser His Gly Ser Gln Asp
            20                  25                  30

Leu Phe Pro Thr Met Leu Thr Ser Gln Tyr Gln Phe Ser Ala Asp Ala
        35                  40                  45

Ser Thr Val
    50

<210> SEQ ID NO 43
<211> LENGTH: 51
<212> TYPE: PRT
<213> ORGANISM: Neurospora crassa

<400> SEQUENCE: 43

Glu Gly Lys Val Ala Ile Lys Lys His Trp Leu Ile Leu Ile Tyr Leu
1               5                   10                  15

Val Leu Leu Trp Ala Gly Phe Asn Phe Met Ser His Gly Ser Gln Asp
            20                  25                  30

Leu Tyr Pro Thr Met Leu Arg Ser Gln Tyr Ser Phe Ser Ala Asn Ala
        35                  40                  45

Val Thr Val
    50

<210> SEQ ID NO 44
<211> LENGTH: 51
<212> TYPE: PRT
<213> ORGANISM: Yarrowia lipolytica
```

```
<400> SEQUENCE: 44

Gly Ile Lys Thr Thr Phe Lys Thr Tyr Trp Leu Met Phe Ile Tyr Leu
1               5                   10                  15

Val Val Leu Trp Ala Gly Phe Asn Phe Met Ser His Gly Ser Gln Asp
            20                  25                  30

Leu Tyr Pro Thr Met Leu Lys Val Gln Leu Gly Phe Ser Pro Asp Arg
        35                  40                  45

Ser Thr Val
    50

<210> SEQ ID NO 45
<211> LENGTH: 51
<212> TYPE: PRT
<213> ORGANISM: Yarrowia lipolytica

<400> SEQUENCE: 45

Gly Val Gly His Thr Leu Lys Val His Trp Leu Met Phe Thr Tyr Leu
1               5                   10                  15

Val Val Met Met Ala Gly Phe Asn Phe Trp Ala His Gly Ser Gln Asp
            20                  25                  30

Leu Tyr Pro Thr Leu Leu Lys Asn Gln Leu Lys Phe Ser Ile Asp Arg
        35                  40                  45

Ser Thr Val
    50

<210> SEQ ID NO 46
<211> LENGTH: 51
<212> TYPE: PRT
<213> ORGANISM: Debaryomyces hansenii

<400> SEQUENCE: 46

Lys Ala Ala Lys Val Leu Lys Tyr Tyr Trp Leu Met Leu Val Tyr Met
1               5                   10                  15

Val Leu Leu Met Ala Gly Phe Asn Phe Met Ser His Gly Ser Gln Asp
            20                  25                  30

Leu Tyr Pro Thr Phe Leu Lys Lys Gln Leu Glu Phe Ser Asp Asp Lys
        35                  40                  45

Ser Thr Val
    50

<210> SEQ ID NO 47
<211> LENGTH: 51
<212> TYPE: PRT
<213> ORGANISM: Lachancea thermotolerans

<400> SEQUENCE: 47

Asn Val Lys Val Ala Leu Ile Gln His Trp Met Thr Leu Val Tyr Leu
1               5                   10                  15

Val Ile Leu Met Ala Met Phe Asn Phe Ser Ser His Gly Ser Gln Asp
            20                  25                  30

Leu Phe Pro Thr Met Leu Thr Asn Gln Tyr Asn Tyr Ser Asp Asp Ala
        35                  40                  45

Ser Thr Val
    50

<210> SEQ ID NO 48
<211> LENGTH: 51
<212> TYPE: PRT
```

<213> ORGANISM: Yarrowia lipolytica

<400> SEQUENCE: 48

Gly Val Lys Thr Thr Phe Lys Ser Tyr Trp Leu Met Phe Phe Tyr Leu
1               5                   10                  15

Val Leu Phe Met Thr Gly Phe Asn Phe Leu Ser His Gly Ser Gln Asp
            20                  25                  30

Leu Tyr Pro Thr Met Leu Arg Ala Gln Leu Gly Phe Asp Lys Asp Gln
        35                  40                  45

Phe Thr Ile
    50

<210> SEQ ID NO 49
<211> LENGTH: 51
<212> TYPE: PRT
<213> ORGANISM: Yarrowia lipolytica

<400> SEQUENCE: 49

Gly Leu Lys Thr Thr Phe Ser Thr Tyr Trp Leu Thr Phe Ile Tyr Leu
1               5                   10                  15

Val Ile Leu Met Ser Gly Phe Asn Phe Met Ser His Gly Ser Gln Asp
            20                  25                  30

Leu Tyr Pro Thr Arg Leu Lys Asn Gln Leu Glu Phe Ser Pro Asp Ala
        35                  40                  45

Ser Thr Val
    50

<210> SEQ ID NO 50
<211> LENGTH: 51
<212> TYPE: PRT
<213> ORGANISM: Yarrowia lipolytica

<400> SEQUENCE: 50

Gly Ile Lys Met Thr Phe Lys Thr Tyr Trp Leu Met Phe Ala Tyr Leu
1               5                   10                  15

Val Val Leu Met Gly Gly Phe Asn Phe Met Ser His Gly Ser Gln Asp
            20                  25                  30

Leu Tyr Pro Thr Met Leu Lys Lys Gln Leu Gly Phe Ser Glu Asp Arg
        35                  40                  45

Ser Thr Val
    50

<210> SEQ ID NO 51
<211> LENGTH: 50
<212> TYPE: PRT
<213> ORGANISM: Neurospora crassa

<400> SEQUENCE: 51

Glu Thr Lys Val Met Leu Arg Gln Glu Trp Lys Met Cys Val Tyr Cys
1               5                   10                  15

Cys Ile Leu Met Thr Trp Phe Asn Cys Asn His Thr Ser Gln Asp Asn
            20                  25                  30

Tyr Thr Thr Phe Val Leu Arg Ala Lys Glu Met Asp Asn Ser Ala Ala
        35                  40                  45

Ser Arg
    50

<210> SEQ ID NO 52
<211> LENGTH: 51

```
<212> TYPE: PRT
<213> ORGANISM: Aspergillus fumigatus

<400> SEQUENCE: 52

Glu Gly Lys Val Ala Leu Lys Arg His Trp Leu Leu Leu Ile Tyr Leu
1               5                   10                  15

Val Leu Leu Trp Ala Gly Phe Asn Phe Met Ser His Gly Ser Gln Asp
            20                  25                  30

Leu Tyr Pro Thr Met Leu Thr Asn Gln Phe Arg Phe Ser Ser Asn Ala
        35                  40                  45

Val Thr Val
    50

<210> SEQ ID NO 53
<211> LENGTH: 51
<212> TYPE: PRT
<213> ORGANISM: Aspergillus nidulans

<400> SEQUENCE: 53

Glu Gly Lys Val Ala Leu Lys Arg His Trp Leu Leu Leu Ile Tyr Leu
1               5                   10                  15

Val Leu Leu Met Ala Gly Phe Asn Phe Met Ser His Gly Ser Gln Asp
            20                  25                  30

Leu Tyr Pro Thr Leu Val Gln Arg Gln Tyr Gly Phe Ser Arg Asp Ala
        35                  40                  45

Val Thr Val
    50

<210> SEQ ID NO 54
<211> LENGTH: 51
<212> TYPE: PRT
<213> ORGANISM: Aspergillus nidulans

<400> SEQUENCE: 54

Glu Thr Lys Val Met Val Gly Gln Glu Trp Lys Ile Cys Val Tyr Cys
1               5                   10                  15

Ile Phe Leu Met Thr Trp Phe Asn Tyr Tyr Ser His Thr Ser Gln Asp
            20                  25                  30

Ser Tyr Thr Thr Phe Met Leu Thr Gln Lys Glu Leu Glu Asn Ser Gly
        35                  40                  45

Ala Ser Arg
    50

<210> SEQ ID NO 55
<211> LENGTH: 51
<212> TYPE: PRT
<213> ORGANISM: Eremothecium gossypii

<400> SEQUENCE: 55

Gln Ile Leu Gln Ser Leu Lys Lys Glu Trp Tyr Ile Val Leu Tyr Met
1               5                   10                  15

Ile Phe Leu Met Thr Ala Tyr Asn Phe Phe Ala His Thr Ser Gln Asp
            20                  25                  30

Leu Phe Pro Thr Met Leu Leu Arg Gln Leu Gly Tyr Thr Pro Asn Gln
        35                  40                  45

Ser Thr Val
    50
```

GENETICALLY ENGINEERED YARROWIA LIPOLYTICA WITH ENHANCED EXTRACELLULAR SECRETION OF α-KETOGLUTARATE

CROSS-REFERENCES AND RELATED APPLICATIONS

This application claims the benefit of priority to Chinese Application No. 201310481832.5, entitled "A Genetically Engineered *Yarrowia Lipolytica* with Enhanced Extracellular Secretion of α-ketoglutarate", filed Oct. 15, 2013, which is herein incorporated by reference in its entirety.

BACKGROUND OF THE INVENTION

1. Field of the Invention

The present invention relates to the field of metabolic engineering, and more particularly relates to a genetically engineered strain of *Yarrowia lipolytica* with enhanced extracellular secretion of α-ketoglutarate.

2. Description of the Related Art

As one of important intermediates in tricarboxylic acid cycle, α-ketoglutaric acid (α-KG) not only plays a key role in metabolic processes of microorganism, such as energy metabolism and synthesis of amino acids, proteins and vitamins, but also plays an important role in the regulation of Carbon/Nitrogen metabolic balance in microorganisms. It is important for study of regulation mechanism of nitrogen metabolism in microbes. As an essential intermediate in fine chemicals and pharmaceutical industry, α-KG is widely used in the synthesis of amino acids, vitamins and other small molecules, and has a wide range of applications in pharmaceutics, organic synthesis and nutritional supplement synthesis.

Due to the special role of α-KG in intracellular metabolism of microbes, when a large amount of α-KG is produced by screened strains during fermentation, it is unaviodable that a large amount of metabolism by-products, such as pyruvic acid, will accumulate in the final fermentation period. Short chain keto acids such as α-KG and pyruvic acid are weak electrolytes which exist in the form of neutral molecular or anion depending on the pH. As intercellular pH is higher than $pK_a$ of α-KG, α-KG and other organic acids predominately exist in their anion state. Excessive anions in cytoplasm result in the acidification of cytoplasm and interruption of cell metabolism. It is therefore necessary for α-KG in anion state to be transported cross cytoplasmic membranes by carboxylic acid transporter. However, when cells lack carbon source, carboxylic acid transporter will also need to transport specific carboxylates into cell as new carbon sources. Other carboxylic acids related to central metabolic pathway have similar secretion and absorption process. Therefore, the kinetic characteristics and regulation mechanism of specific carboxylic acid transporters located at cell membrane play a important role in regulating accumulation of carboxylic acids inside cells and in the fermentation broth.

DETAILED DESCRIPTION

The goal of the present invention is to provide a genetically engineered *Yarrowia lipolytica* (*Y. lipolytica*) WSH-Z06 with high levels of extracellular α-KG expression, which over-expresses one or more keto acid transporter genes.

The nucleotide sequences of the above mentioned keto acid transporter genes are the following:

(1) a nucleotide sequence of SEQ ID NO:1 (NCBI's accession number: XM_501098.1, gene locus_tag: YALI0B19470g) (Seq ID NO:1),
(2) a nucleotide sequence of SEQ ID NO:3 (NCBI's accession number: XM_502090.1, gene locus_tag: YALI0C21406g) (Seq ID NO:3),
(3) a nucleotide sequence of SEQ ID NO:4 (NCBI's accession number: XM_503058.1, gene locus_tag: YALI0D20108g) (Seq ID NO:4),
(4) a nucleotide sequence of SEQ ID NO:6 (NCBI's accession number: XM_504706.1, gene locus_tag: YALI0E32901g) (Seq ID NO:6).

In a preferred embodiment, the gene encoded by the nucleic acid of Seq ID NO:1 is over-expressed in *Yarrowia lipolytica* WSH-Z06, which results in increased levels of extracellular α-KG and decreased levels of extracellular pyruvic acid.

The *Yarrowia lipolytica* WSH-Z06 was obtained from China center for type culture collection (CCTCC) with CCTCC NO: M207140.

The method for constructing the genetically engineered strains comprises the following steps:
(1) Constructing an integrative expression plasmid p0(hph) using hygromycin phosphotransferase as a selectable marker gene;
(2) Constructing a recombinant expression plasmid: synthesize the open reading frame (ORF) of putative keto acid transporter by total chemical synthesis based on the published nucleotide sequence by NCBI; digest the keto acid transporter ORF and the integrative plasmid p0(hph) at the same time using restriction enzyme Bam HI and Eco RI (or Not I and Eco RI) and connect the digested fragments of keto acid transporter ORF and p0(hph) to obtain a recombinant expression plasmid with the keto acid transporter ORF integrative into p0(hph) plasmid;
(3) Transforming the recombinant expression plasmid into *Y. lipolytica* WSH-Z06: linearize the recombinant expression plasmid using the restriction enzyme Avr II, transform linearized recombinant expression plasmid into *Y. lipolytica* WSH-Z06 using an electroporation method, and screen for and validate positive transformants.

The method for producing α-KG using the genetically engineered strain is as follows:

The genetically engineered strain containing the recombinant expression plasmid is inoculated into a seed culture medium, and cultured at 28° C., 200 rpm for 16-18 hours. The cultured cells were inoculated into 3 L fermentor with an inoculum size of 10% (v/v), and cultured at 28° C., 400 rpm for 144-168 hours with an aeration rate of 1.5 vvm.

Compared with a control group without overexpressing a putative keto acid transporter, the extracellular concentration of α-KG of the recombinant strains over-expressing genes of Seq ID NO: 1, Seq ID NO: 3, Seq ID NO: 4 and Seq ID NO: 6 increased from 16.6 g/L to 26.7, 18.6, 24.0 and 19.0 g/L, respectively.

The present invention provides four keto acid transporter genes which are able to increase extracellular expression of α-KG in *Y. lipolytica* cells. The present invention further provides *Y. lipolytica* cells transformed with one or more of the four keto acid transporter genes, which have enhanced extracellular expression of α-KG. Increasing extracellular expression of α-KG can simplify the downstream isolation and purification process, reduce the operation cost and increase the final yield.

*lipolytica* cells. A, Changes of intracellular pyruvic acid(○) and α-KG(Δ) concentration using pyruvic acid and α-KG as the only carbon source, respectively; B, Changes of expression levels of putative keto acid transporter using pyruvic acid (gray bar) or α-KG (black bar) as the only carbon source.

FIG. 2. Homology analysis of putative keto acid transporters. The putative keto acid transporters are A0090005000420 (SEQ ID NO:29), Q75E76 (SEQ ID NO:30), Q4X1M4 (SEQ ID NO:31), Q75E88 (SEQ ID NO:32, Q70DJ7 (SEQ ID NO:33), P36035 (SEQ ID NO:34), Q6BL03 (SEQ ID NO:35), Q6BJV3 (SEQ ID NO:36), Q5A2W4 (SEQ ID NO:37), Q5A5U2 (SEQ ID NO:38), YALI0E32901p (SEQ ID NO:39), Q4WB22 (SEQ ID NO:40), A0090011000744 (SEQ ID NO:41), Q70IQ9 (SEQ ID NO:42), Q7SB47 (SEQ ID NO:43), YALI0C15488p (SEQ ID NO:44), YALI0B19470p (SEQ ID NO:45), Q6BR62 (SEQ ID NO:46), KLTH0G02024g (SEQ ID NO:47), YALI0C21406p (SEQ ID NO:48), YALI0D24607p (SEQ ID NO:49), YALI0D20108p (SEQ ID NO:50), Q9P732 (SEQ ID NO:51), Q4WGM5 (SEQ ID NO:52), AN6703-2 (SEQ ID NO:53), AN6095.2 (SEQ ID NO:54), and Q753H9 (SEQ ID NO:55).

Figure 3:
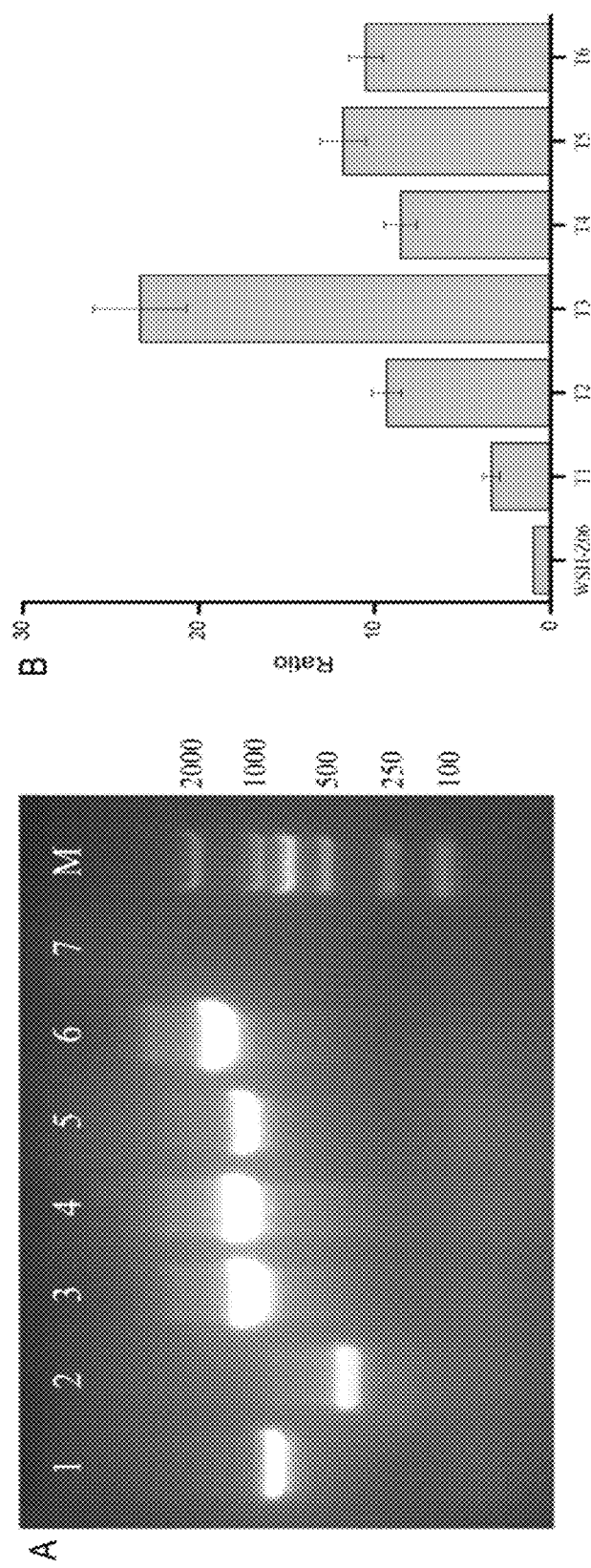

FIG. 3. Verification of overexpression of the putative keto acid transporters in recombinant *Y. lipolytica* WSH-Z06 cells. A, Electrophoresis of PCR products using genomic DNAs as templates (PCR primers in Table 1). Panel 1: *Y. lipolytica* T1 (Seq ID NO. 4), Panel 2: *Y. lipolytica* T2 (Seq ID NO. 3), Panel 3: *Y. lipolytica* T3 (Seq ID NO. 1), Panel 4: *Y. lipolytica* T4 (Seq ID NO. 2), Panel 5: *Y. lipolytica* T5 (Seq ID NO. 5), Panel 6: *Y. lipolytica* T6 (Seq ID NO. 6), Panel 7: negative control (ultrapure water). B, Verification of mRNA levels of each keto acid transporter in the recombinant strains (PCR primers in Table 2). The ratio is calculated as mRNA level of each transporter in the transporter-overexpressing recombinant strain over that of the wild type strain.

Figure 4:
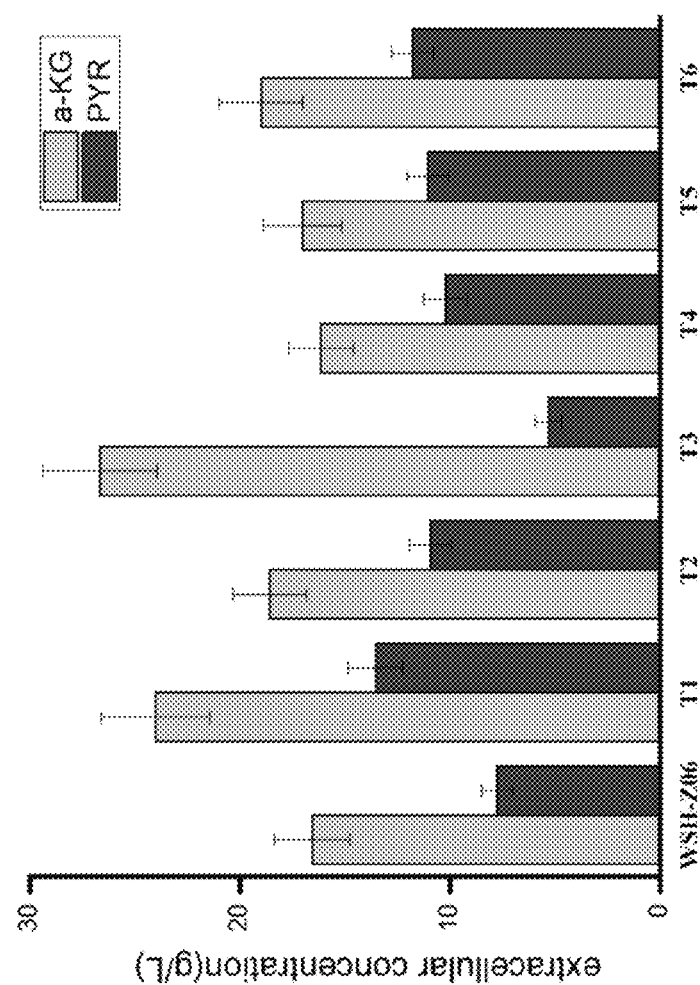

FIG. 4. Extracellular keto acid concentrations of recombinant *Y. lipolytica* strains using α-KG or pyruvic acid as the only carbon source.

Table 1. Oligonucleotide primers used for verification of integration of the transporter genes into the host genome.

Table 2. Oligonucleotide primers used for qPCR to measure mRNA levels in transporter-overexpressing recombinant strains.

EXAMPLES

Materials and Methods

YPD medium: 10 g·L$^{-1}$ yeast extract, 20 g·L$^{-1}$ peptone, 20 g·L$^{-1}$ dextrose. To make solid medium, add 20 g·L$^{-1}$ Agar. Hygromycin B was added to the concentration of 400 m g·L$^{-1}$ during the selection of transformants.

YPK medium: 100 g·L$^{-1}$ α-KG, 1.7 g·L$^{-1}$ yeast nitrogen base, and 5 g·L$^{-1}$ (NH$_4$)$_2$SO$_4$, pH=5.0.

YPP medium: 50 g·L$^{-1}$ pyruvate, 1.7 g·L$^{-1}$ yeast nitrogen base, and 5 g·L$^{-1}$ (NH$_4$)$_2$SO$_4$, pH=5.0

Seed medium: 20 g·L$^{-1}$ glucose, 10 g·L$^{-1}$ peptone, 1 g·L$^{-1}$ KH$_2$PO$_4$, 0.5 g·L$^{-1}$ MgSO$_4$·7H$_2$O, pH=5.5. To make solid medium, add 20 g·L$^{-1}$ agar. The sterilization was performed at 115° C. for 15 minutes.

Fermentation medium: 100 g·L$^{-1}$ glycerol, 3 g·L$^{-1}$ (NH$_4$)$_2$SO$_4$, 3 g·L$^{-1}$ KH$_2$PO$_4$, 1.2 g·L$^{-1}$ MgSO$_4$·7H$_2$O, 0.1 g·L$^{-1}$ K$_2$HPO$_4$, 0.5 g·L$^{-1}$ NaCl, 2×10$^{-7}$ g·L$^{-1}$ thiamine pH=4.5. The sterilization was performed at 115° C. for 15 minutes. 20 g·L$^{-1}$ CaCO$_3$ was added as a neutralizing agent before inoculation.

The *Yarrowia lipolytica* WSH-Z06 was obtained from China Center for Type Culture Collection (CCTCC) with CCTCC NO: M20714.

Determination of extracellular keto acid concentration: fermentation samples were centrifuged at 12000 g for 5 minutes. The supernatant was diluted 50 times with ultrapure water, and keto acid concentration of the sample was determined using HPLC.

Determination of intercellular keto acid concentration: cells were collected by centrifugation, and washed by 0.9% physiological saline. Cell were resuspended in 10 mL buffer solution containing 0.1 mol·L$^{-1}$ KH$_2$PO$_4$—K$_2$HPO$_4$, 1 mmol·L$^{-1}$ EDTA, 0.01 mmol·L$^{-1}$ DTT (pH 7.5). After addition of one volume of acid-washed quartz sand, cells were disrupted by a vortex mixer for 5 minutes, and centrifuged at 13,000 g for 10 minutes to remove the precipitation. 5 ml supernatant was filtered through a membrane with a pore size 0.22 μm. The concentration of keto acid in the supernatant was then measured using HPLC.

Conditions for HPLC analysis: α-KG and pyruvate were simultaneously determined by HPLC (Agilent 1200 series, Santa Clara, Calif.) with a Aminex HPX-87H ion exchange column (300 mm×7.8 mm; Bio-Rad Laboratories Inc., Hercules, Calif.). The mobile phase was 5 mmol·L$^{-1}$ sulfuric acid in distilled, de-ionized water filtered through a 0.22 μm pore size membrane. The mobile phase flow rate was 0.6 mL·min$^{-1}$. The column temperature was maintained at 35° C., and the injection volume was 10 μL. The α-KG and pyruvate were detected by UV (wavelength at 210 nm) detector.

Transformation of *Yarrowia lipolytica*: A freshly grown single colony of *Yarrowia lipolytica* WSH-Z06 cells were transferred into liquid YPD medium and cultured at 28° C., 200 rpm overnight. The *Yarrowia lipolytica* WSH-Z06 cells were transferred into new liquid YPD medium by an inoculum size of 10% (v/v), cultured at 28° C., 200 rpm until the OD$_{600}$=1.2. The cells were collected by centrifugation, and resuspended at 8×10$^8$ cells/mL in 8 mL buffer solution (100 mmol·L$^{-1}$ LiAc, 10 mmol·L$^{-1}$ DTT, 0.6 mol·L$^{-1}$ sorbitol 10 mmol·L$^{-1}$ Tris-HCL, pH=7.5) and incubated at 30° C. for 30 minutes. Collect cells again by centrifugation and wash the cells by ice-chilled 5 mL 1 mol·L$^{-1}$ sorbitol solution three times, and resuspend cells to the concentration of 10$^{10}$ cell·mL$^{-1}$ in the sorbitol solution. The linearized integrative recombinant plasmid was added to the cell suspension, incubated on ice for 5 min, and transferred to a ice-chilled 0.2-cm electric rotor. The electroporation shock was performed at 2.5 KV, 25 μF, 200Ω, and 1 mL ice-chilled 1 M sorbitol solution was immediately added afterwards. The mixture was incubated at room temperature for 1 h. 0.2 mL cells, which have been electrically shocked, were spread on the selective culture plates with 400 mg·L$^{-1}$ Hygromycin B, and cultured at 28° C. for 48-72 hours.

Example 1

Screening for Putative Keto Acid Transporter Genes and Analysis of Conserved Sequences The method of screening for keto acid transporter genes comprises the following steps:
1. 6611 protein sequences of *Y. lipolytica* CUB 122 database were obtained from UniProt;
2. TMHMM is used to analyze transmembrane topology of these proteins and screen for putative transporter proteins. The putative transporter proteins are selected according to two criteria: (i) the number of residues in predicted transmembrane helices is more than 18; (ii) the number of predicted transmembrane helices is more than one. There are 1104 putative transporter protein sequences selected based on these selection criteria.

(3) 117 sequences of the above transporter proteins were predicted to be signal peptides using SignalP, and thus were removed from further consideration.

(4) The remaining putative transporter protein sequences were aligned with reference sequences, single keto acid transporter SACE0K00242g from *Saccharomyces cerevisiae* and double keto acid transporter KLLA0F10043g from *Kluyveromyces lactis*, using Blast software. Six transporter protein sequences with more than 30% sequence homology with the reference sequences were selected as putative keto acid transporters of *Y. lipolytica* strain. The complete cDNA sequences encoding the six putative keto acid transporter proteins are identified as the following: Seq ID NO: 1 (NCBI's accession number: XM_501098.1, gene locus_tags YALI0B19470g) (Seq ID NO:1), Seq ID NO: 2 (NCBI's accession number: XM_501871.0, gene locus_tags YALI0C15488g) (Seq ID NO:2), Seq ID NO: 3 (NCBI's accession number: XM_502090.1, gene locus_tag: YALI0C21406g) (Seq ID NO:3), Seq ID NO: 4 (NCBI's accession number: XM_503058.1, gene locus_tag: YALI0D20108g) (Seq ID NO:4), Seq ID NO: 5 (NCBI's accession number: XM_503239.1, gene locus_tag: YALI0D24607g) (Seq ID NO:5) and Seq ID NO: 6 (NCBI's accession number: XM_504706.1, gene locus_tag: YALI0E32901g) (Seq ID NO:6), which have sequence homology of 37%, 40%, 41%, 42%, 43%, 39% with SACE0K00242g (*Saccharomyces cerevisiae*) and 46%, 53%, 49%, 52%, 51%, 51% with KLLA0F10043g (*Kluyveromyces lactis*), respectively.

(5) Keto acid transporting activity of the six putative keto acid transporters was validated by quantitative real-time PCR, when the genes were transformed into *Y. lipolytica* cells, and the transformed cells were cultured in YPP or YPK medium using pyruvic acid or α-KG as the only carbon source.

Figure 1:
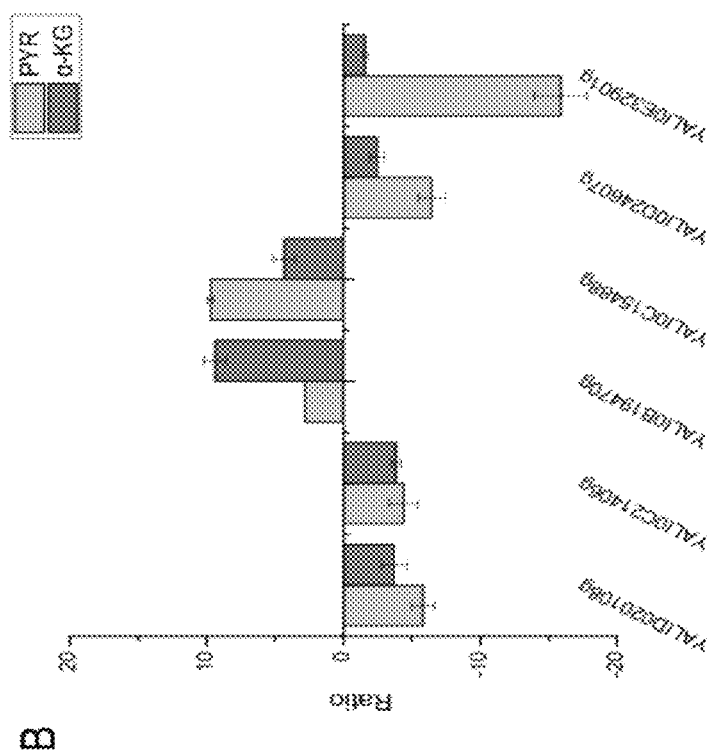
FIG. 1. Changes of intracellular carboxylates and expression of the putative keto acid transporters in wild type *Y.*
Figure 1:
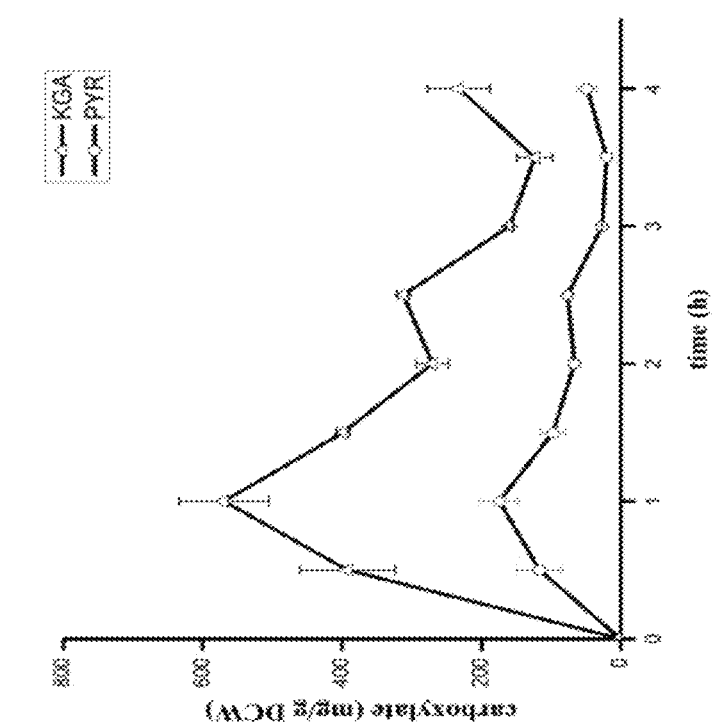

The experimental results showed that the intracellular pyruvic acid and α-KG level was the highest in the first hour of cultivation when wild type *Y. lipolytica* cells were cultured in the medium using pyruvic acid or α-KG as the only carbon source (FIG. 1A).

Compared with the control cells cultured in YPD medium, cells cultured in YPP medium (using pyruvic acid as the only carbon source) have expression levels of YALI0B19470g (Seq. ID NO:1) and YALI0C15488g (Seq. ID NO:2) increased 2.8 and 9.7 fold, respectively, whereas the expression of YALI0C21406g (Seq. ID NO:3), YALI0D20108g (Seq. ID NO:4), YALI0D24607g (Seq. ID NO:5) and YALI0E32901g (Seq. ID NO:6) decreased 4.4, 5.8, 6.4 and 15.9 fold, respectively. Compared with the control cells cultured in YPD medium, cells cultured in YPK medium (using α-KG as the only carbon source) have expression levels of YALI0B19470g (Seq. ID NO:1) and YALI0C15488g (Seq. ID NO:2) increased 9.4 and 4.3 fold, respectively, whereas expression levels of YALI0C21406g (Seq. ID NO:3), YALI0D20108g (Seq. ID NO:4), YALI0D24607g (Seq. ID NO:5) and YALI0E32901g (Seq. ID NO:6) decreased 3.9, 3.7, 2.5 and 1.6 fold, respectively (FIG. 1B). These data indicated that the expression of these putative keto acid transporter genes are regulated by carboxylic acids.

The six putative keto acid transporters in *Y. lipolytica*, YALI0B19470g, YALI0C15488g, YALI0C21406g, YALI0D20108g, YALI0D24607g and YALI0E32901g, were aligned with 21 known keto acid transporters from ten other fungoids using the software ClustalX2. The protein sequence alignment showed that all of 27 keto acid transporters sequences have the consensus residues (SEQ ID NO:28) NXX[S/T]HX[S/T]QDXXXT (FIG. 2), which is located at the seventh transmembrane region of YALI0B19470g, YALI0C15488g, YALI0C21406g, YALI0D20108g, YALI0D24607g and YALI0E32901g.

Example 2

The Construction and Characterization of Recombinant *Yarrowia lipolytica* Strains Construction of p0(hph) integrative expression vector: PCR primers were designed and hygromycin phosphotransferase gene (hph) gene were amplified from pUB4-CRE plasmid. The amplified hph gene and p0 integrative plasmid (Zhou, J. W., X. X. Yin, et al. (2012). "Enhanced α-ketoglutarate production in *Yarrowia lipolytica* WSH-Z06 by alteration of the acetyl-CoA metabolism." *Journal of Biotechnology* 161(3): 257-264) were digested by restriction enzyme Stu I and Hind III at the same time, and linked together to make an integrative expression vector p0(hph) with hygromycin phosphotransferase gene as a selection marker.

The complete open reading frame sequences (ORFs) of all the putative transporter genes were chemical synthesized. The p0(hph) plasmid and ORFs of YALI0B19470g (Seq. ID NO:1), YALI0C15488g (Seq. ID NO:2), YALI0D20108g (Seq. ID NO:4), YALI0D24607g (Seq. ID NO:5) and YALI0E32901g (Seq. ID NO:6) were digested by Eco RI and Bam HI, and were ligated together to make integrative express vectors p0(hph) containing transporter ORFs, resulting in plasmid p0(hph)-470, p0(hph)-488, p0(hph)-108, p0(hph)-607 and p0(hph)-901, respectively. The p0(hph) plasmid and the ORF of YALI0C21406g (Seq. ID NO:3) were digested by Not I and Eco RI, and were ligated together to make the integrative express vector p0(hph)-406.

All the six integrative expression vectors were linearized by Avr II and purified before transformation. The linearized vector fragments were transformed into *Y. lipolytica* WSH-Z06 using electroporation method as described above. The positive transformants were selected in YPD medium plates containing 400 mg·L$^{-1}$ hygromycin B. Using primer pairs with a forward primer specific for a promoter sequence in p0(php) plasmid (VBF primer, Table 1) and a reverse primer specific for each of six putative keto acid transporters (primer V108, V406, V470, V488, V607 and V901, Table 1), a PCR was performed against genomic DNAs of positive transformants to determine if the ORFs of the transporters have been actually integrated into the genomic DNAs. As a result, six positive transformants with the transporter ORF sequences integrated into their genomes were identified and designated as *Y. lipolytica* T1, T2, T3, T4, T5 and T6 for the six transporter genes of YALI0D20108g (Seq. ID NO:4), YALI0C21406g (Seq. ID NO:3), YALI0B19470g (Seq. ID NO:1), YALI0C15488g (Seq. ID NO:2), YALI0D24607g (Seq. ID NO:5) and YALI0E32901g (Seq. ID NO:6), respectively. The six positive transformants and a wild type *Y. lipolytica* WSH-Z06 were cultured in YPD medium, and cells were collected during the exponential growth phase. Using quantitative PCR (qPCR) analysis, the mRNA levels of the transformed transporter genes were measured in the recombinant strains and the wild type strains. The results showed that the fold change of mRNA levels of the transporter genes for *Y. lipolytica* T1, T2, T3, T4, T5 and T6 recombinant strains were 3.4, 9.3, 23.3, 8.5, 11.8 and 10.5, respectively, compared to that of the wild type strain (FIG. 3). The primer pairs used for qPCR analysis are listed in Table 2 with the corresponding gene followed by a letter "F" and "R" referring to a forward and reverse primer, respectively (e.g. YALI0D20108F and YALI0D20108R refer to the forward and reverse primer for gene YALI0D20108, respectively.). The ACT1F and ACT1R refer to the forward and reverse primer of the control gene actin.

Example 3

Verification of the Ability of Recombinant Y. lipolytica Strains to Transport Keto Acids The six recombinant strains lipolytica T1, T2, T3, T4, T5 and T6 were first inoculated into the agar slant containing seed medium, then transferred into 50 mL liquid seed medium in a 500 mL flask, and cultured at 28° C., 200 rpm for 16-18 hours. The cultured cells were inoculated into fermentation medium with a 10% (v/v) inoculum size, and cultured at 28° C., 200 rpm for 144-168 hours. The overexpression results showed that extracellular concentration of α-KG produced by recombinant strains lipolytica T1, T2, T3 and T6 increased to 24.0, 18.6, 26.7, and 19.0 g·L$^{-1}$ from 16.6 g·L$^{-1}$ of the wild type strain. However, the extracellular concentration of α-KG produced by recombinant strains lipolytica T4 and T5 had no significant change (FIG. 4).

The extracellular concentration of pyruvic acid produced by recombinant strains lipolytica T1, T2, T4, T5 and T6 increased to 13.5, 11.0, 10.2, 11.0 and 11.8 g·L$^{-1}$, respectively, from 7.8 g·L$^{-1}$ of the wild type strain. On the contrary, the extracellular concentration of pyruvic acid produced by Y. lipolytica T3 decreased to 5.3 g·L$^{-1}$ from 7.8 g·L$^{-1}$ (FIG. 4).

Compared with the control wild type strain, the ratio of extracellular α-KG to pyruvic acid produced by Y. lipolytica T1, T2, T3, T4, T5 and T6 changed from 2.1 to 1.8, 1.7, 5.0, 1.6, 1.5 and 1.6, respectively.

The present invention provides six keto acid transporter genes of Y. lipolytica strains: YALI0D20108g (Seq. ID NO:4), YALI0C21406g (Seq. ID NO:3), YALI0B19470g (Seq. ID NO:1), YALI0C15488g (Seq. ID NO:2), YALI0D24607g (Seq. ID NO:5) and YALI0E32901g (Seq. ID NO:6), and the corresponding recombinant strains designated as Y. lipolytica T1, T2, T3, T4, T5 and T6, respectively. All of the six identified transporter genes have the conserved amino acid sequences critical for the keto acid transporting activity. The expression levels of these six identified transporter genes were similarly regulated by pyruvic acid and α-KG. Two of the transporter genes, YALI0B19470g (Seq. ID NO:1) and YALI0C15488g (Seq. ID NO:2), are up-regulated by both pyruvic acid and α-KG. Four of the transporter genes, YALI0D20108g (Seq. ID NO:4), YALI0C21406g (Seq. ID NO:3), YALI0D24607g (Seq. ID NO:5) and YALI0E32901g (Seq. ID NO:6), are down-regulated by both pyruvic acid and α-KG. These data suggest that pyruvic acid and α-KG might regulate the expression of these genes in similar mechanisms. Overexpressing genes YALI0D20108g (Seq. ID NO:4), YALI0C21406g (Seq. ID NO:3) and YALI0E32901g (Seq. ID NO:6) leads to enhanced expression of both pyruvic acid and α-KG, suggesting that these genes are multi-transporter that are able to transport these two keto acids. Overexpressing genes YALI0C15488g (Seq. ID NO:2) and YALI0D24607g (Seq. ID NO:5) lead to significant increase of extracellular pyruvic acid, but not α-KG, suggesting that these two transporters preferably transport pyruvic acid. The transporter encoded by YALI0B19470g (Seq. ID NO:1) is unique in that it increases extracellular level α-KG while decreases extracellular level of pyruic acid. Therefore, YALI0B19470g (Seq. ID NO:1) encoding keto acid transporter is a preferable choice for keto acid production.

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

TABLE 1

Oligonucleotide primers used for verification of integration of the transporter genes into the host genome.

| Primers | Sequence (5'-3') |
| --- | --- |
| VBF (Seq ID NO: 21) | CGTTTGCCAGCCACAGATT |
| V108 (Seq ID NO: 22) | GCGTTTGCCAGCCACAGAT |
| V406 (Seq ID NO: 23) | GTAGATGCAGGCAGCACCG |
| V470 (Seq ID NO: 24) | AAGACAGAGGCGTTGATACCG |
| V488 (Seq ID NO: 25) | TGCGAGGTTACCAAGCTGAT |
| V607 (Seq ID NO: 26) | GACAAACGCCCAGGGATAG |
| V901 (Seq ID NO: 27) | TGTCCATCTGCTTGCCCTC |

TABLE 2

Oligonucleotide primers used for qPCR to measure mRNA levels in transporter-overexpressing recombinant strains.

| Primers | Sequence (5'-3') |
| --- | --- |
| YALI0B19470F (Seq ID NO: 7) | CAACAAGGAAGACAACAG |
| YALI0B19470R (Seq ID NO: 8) | AGGTAGGTGAACATAAGC |
| YALI0C15488F (Seq ID NO: 9) | GCAACCATCTCAGCCATTC |
| YALI0C15488R (Seq ID NO: 10) | GTAACCTCGCATCTTCAGC |
| YALI0C21406F (Seq ID NO: 11) | GCAGACCTACCAGCAGTTC |
| YALI0C21406R (Seq ID NO: 12) | ACGACACAGAGCAAGTATCC |
| YALI0D20108F (Seq ID NO: 13) | TGCTACAGGAAGGCTATGC |
| YALI0D20108R (Seq ID NO: 14) | GGAAGATGATGATGAGAACAGG |
| YALI0D24607F (Seq ID NO: 15) | CTGCTTGTAGGTGGTGAC |
| YALI0D24607R (Seq ID NO: 16) | GAGTGCTGAGTGATAAATACG |
| YALI0E32901F (Seq ID NO: 17) | TCTATGATTACGGTAAGGTTATG |
| YALI0E32901R (Seq ID NO: 18) | GACTCGCTCAAGGTTCTC |
| ACT1F (Seq ID NO: 19) | AAGTCCAACCGAGAGAAGATG |
| ACT1R (Seq ID NO: 20) | ACCAGAGTCAAGAACGATACC |

What is claimed is:

1. A genetically engineered *Yarrowia lipolytica* strain with enhanced extracellular secretion of α-ketoglutarate as compared to that of a wild type *Yarrowia lipolytica* strain, wherein said genetically engineered *Yarrowia lipolytica* strain overexpresses a keto acid transporter gene comprising a nucleic acid sequence of Seq ID NO: 1.

2. The genetically engineered *Yarrowia lipolytica* strain of claim 1, wherein said genetically engineered *Yarrowia lipolytica* strain further expresses one or more than one genes selected from a group of nucleic acid sequences consisting of:
  1) a nucleic acid sequence of Seq ID NO: 3;
  2) a nucleic acid sequence of Seq ID NO: 4; and
  3) a nucleic acid sequence of Seq ID NO: 6.

3. A method of constructing a recombinant *Yarrowia lipolytica* strain overexpressing a keto acid transporter gene comprising a nucleic acid sequence of Seq ID NO: 1, comprising the steps of:
  1) Constructing an integrative expression plasmid p0(hph) with hygromycin phosphotransferase as a selectable marker gene;
  2) Constructing a recombinant integrative expression plasmid containing said keto acid transporter gene, wherein an open reading frame sequence of said keto acid transporter is chemically synthesized and subcloned into said integrative expression plasmid p0(hph);
  3) Transforming said recombinant expression plasmid into *Y. lipolytica*; and
  4) Screening for a positive transformant with said keto acid transporter gene integrated into its genomic DNA.

4. The method of claim 3, further comprising expressing in said recombinant *Yarrowia* lipolytica strain one or more than one genes selected from a group of nucleic acid sequences consisting of:
  1) a nucleic acid sequence of Seq ID NO: 3;
  2) a nucleic acid sequence of Seq ID NO: 4; and
  3) a nucleic acid sequence of Seq ID NO: 6.

* * * * *